United States Patent [19]
Asbelle et al.

[11] 3,982,280
[45] Sept. 28, 1976

[54] FUNCTIONAL ANKLE FOR A PROSTHETIC LIMB

[75] Inventors: Charles C. Asbelle, Oakland; Gene R. Helmuth, Castro Valley; William R. Applegate; Gerald K. Porter, both of Oakland, all of Calif.

[73] Assignee: The United States of America as represented by the Secretary of the Navy, Washington, D.C.

[22] Filed: Oct. 6, 1975

[21] Appl. No.: 619,873

Related U.S. Application Data

[63] Continuation of Ser. No. 357,049, May 3, 1973, abandoned.

[52] U.S. Cl. ............................................. 3/32; 3/7
[51] Int. Cl.² ........................ A61F 1/04; A61F 1/08
[58] Field of Search ............................ 3/30–35, 3/6, 7

[56] References Cited
UNITED STATES PATENTS
2,594,945   4/1952   Lucas et al. .............................. 3/32

FOREIGN PATENTS OR APPLICATIONS
834,884   3/1952   Germany .................................. 3/32

OTHER PUBLICATIONS

"Human Limbs & Their Substitutes" by Klopsteg & Wilson et al., McGraw–Hill Book Co., Inc., 1954, pp. 497–499, FIGS. 17.7 & 17.8.

Primary Examiner—Ronald L. Frinks
Attorney, Agent, or Firm—R. S. Sciascia; Charles D. B. Curry; James M. Skorich

[57] ABSTRACT

A functional ankle for a prosthetic limb comprising an elastomeric member and a flexible member. The elastomeric member separates the prosthetic foot from the shin. The elastomeric member allows the foot to move relative to the shin while providing plantar/dorsi flexion, inversion/eversion and rotational motion singularly or in combination. The foot and shin are connected by the flexible member which allows relative motion while providing structural integrity.

1 Claim, 3 Drawing Figures

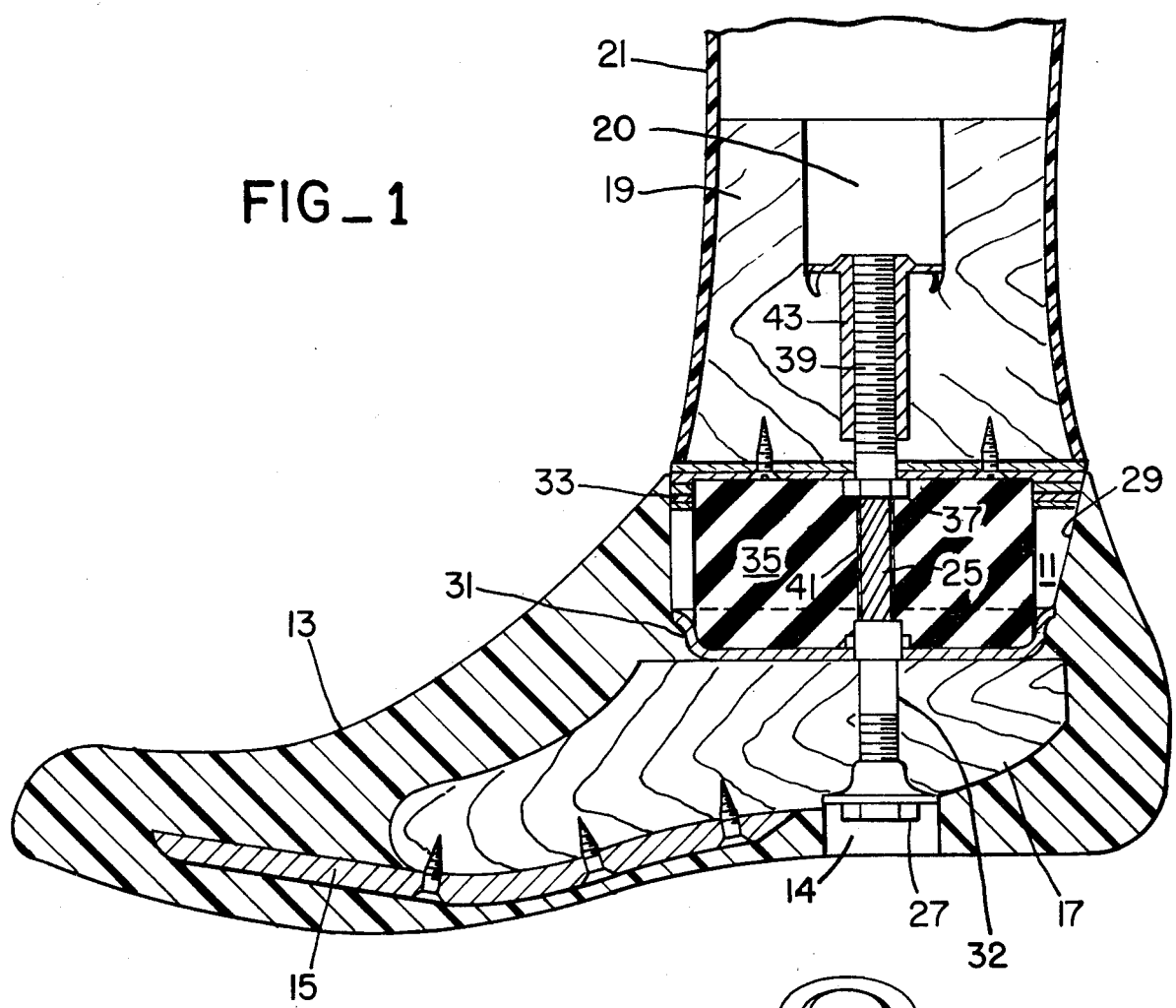
FIG_1
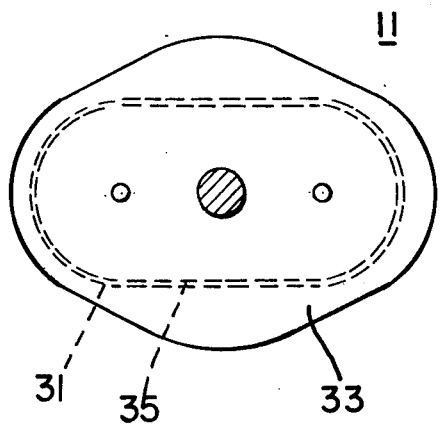
FIG_1B
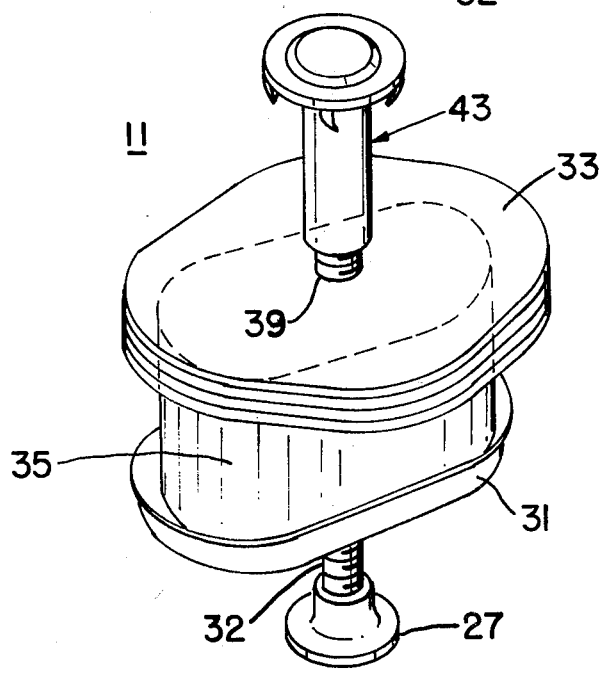
FIG_1A

FUNCTIONAL ANKLE FOR A PROSTHETIC LIMB

This application is a continuation of patent application Ser. No. 357,049 filed May 3, 1973, by Charles A. Asbelle et al., now abandoned.

BACKGROUND OF THE INVENTION

1. Field of the Invention

The subject matter of the present invention relates generally to a functional ankle for a prosthetic limb and more particularly to a functional ankle which supplies the minimum basic motion for an artificial foot of a lower extremity prosthesis.

2. Description of the Prior Art

The present prosthetic devices encompass some form of the solid ankle cushion heel, hereinafter referred to as "SACH", which is comprised of a solid ankle, with no functional movement, which is attached to the foot. In the SACH foot the functional movement is provided by a soft heel that deflects under a load, allowing the foot to adapt to terrain or loads applied by the amputee. Functionally, this foot is inadequate since it does not provide rotation about the long axis of the wearer's leg.

SUMMARY OF THE INVENTION

Briefly, the present invention is a functional ankle for a prosthetic limb comprising an elastomeric member and a flexible member. The elastomeric member separates the prosthetic foot from the shin. The elastomeric member allows the foot to move relative to the shin while providing plantar/dorsi flexion, inversion/eversion and rotational motion singularly or in combination. The foot and shin are connected by the flexible member which allows relative motion while providing structural integrity.

The present invention supplies the minimum basic motion as well as rotation about the long axis of the leg of the wearer.

STATEMENT OF THE OBJECTS OF THE INVENTION

A primary object of the present invention is to provide a functional ankle which supplies the minimum basic motion for an artificial foot of a lower extremity prosthesis.

Another object of the present invention is to provide a functional ankle which allows for rotation about the long axis of the leg of the wearer.

Other objects, advantages and novel features of the invention will become apparent from the following detailed description of the invention when considered in conjunction with the accompanying drawings wherein:

FIG. 1 is a cross-sectional view of the functional ankle device which is attached between a conventional shin block and foot;

FIG. 1A is an isometric representation of the functional ankle device illustrated in FIG. 1, parts broken away to show the internal components; and FIG. 1B is a top sectional view of the ankle device illustrated in FIGS. 1 and 1A.

DESCRIPTION OF THE PREFERRED EMBODIMENTS

Referring to FIGS. 1 and 1A, the functional ankle 11 is comprised of a foot 13, shin 21, flexible ankle cable 25, and elastomeric bumper 35. The foot 13 includes a balata belting 15 and a heel portion 17. The balata belting 15 is attached to the base of heel 17 to prevent the foam material, which forms the foot 13, from deforming. The heel 17 may be made of wood or an equivalent material. A recessed portion 14 in the base of foot 13 provides access space for adjustment of the functional ankle 11. The heel 17 is bored to provide passage for flexible ankle cable 25. The foot 13 is a standard molded foam foot which has been modified to accept the functional ankle 11. The laminated shin 21 is a standard prosthetic shin which has been modified to include shin block 19. Shin block 19 comprises recessed portion 20 and threaded sleeve 43. The upper part of ankle bumper fixture 33 is rigidly attached to the base of shin block 19 and shin block 19 is bored to accept sleeve 43. Sleeve 43 is threaded to accept threaded shank 39, which is fixedly attached using a standard method of attachment to ankle cable 25.

Referring to FIGS. 1, 1A and 1B, flexible ankle 11 is comprised of bumper 35, lower ankle bumper fixture 31, and upper ankle bumper fixture 33. Both fixtures 31 and 33 have been bored to allow the cable 25 to be extended therethrough. The fixture 33 is made elliptical in shape to simulate the cross-sectional shape of a patient's ankle. Ankle cable 25 extends through both fixtures 31 and 33, down through bumper 35, heel 17, and is coupled to threaded shank 32. A threaded adjusting nut 27 is placed on the end of shank 32 so that the tension on ankle cable 25 may be adjusted. Ankle cable 25 is covered with a covering material 41 such as plastic or its equivalent.

In operation the rubber bumper 35 functions as an elastomeric spring separating the foot 13 from the shin 21. The bumper 35, by virtue of its elasticity, allows foot 13 to move relative to shin 21 and provides plantar/dorsi flexion, inversion/eversion, and rotation, singularly or in combination. The foot 13 and shin 21 are held together by a cable 25, which allows the relative motion but provides structural integrity and limited adjustability since cable 25 can preload elastomeric bumper 35.

The bumper 35 may be constructed of any elastomeric material natural or synthetic. The bumper 35 is constructed to fit into cored out section 29 of foot 13. The cable may be of any metal or synthetic material that exhibits suitable physical properties of flexation. However, to protect the cable from corrosion, a corrosive resistant material should be used. The structural elements in the foot 13 and/or shin 21 may be made of any material well known in the art. The requirement of low weight should be balanced against the requirement of durability in the most effective compromise of the total design. The unique functional ankle 11 allows for restoration of function to the ankle joint of an artificial limb while allowing for the use of an acceptable cosmetic envelope. The unique functional ankle is dimensionally interchangeable with commonly used artifical feet, such as the standards and specifications for prosthetic foot/ankle assemblies described in the Veterans Administration publication VAPC-L-7007-1, dated Jan. 1, 1971.

The functional ankle 11 provides the amputee with an ankle that supplies the minimum basic motion for the artificial foot of a lower extremity prosthesis.

What is claimed is:

1. An ankle device for a prosthetic limb comprising:
   a. shin block;
   b. a foot;

c. a cable assembly;
d. a bumper assembly;
e. said bumper assembly including an upper ankle bumper fixture, a lower ankle bumper fixture and an elastomeric bumper;
f. said upper ankle bumper fixture including a top plate and a plurality of supporting plates; said top plate having a length, width and thickness wherein said length is greater than said width and said thickness is substantially less than said width and length; said plurality of support plates having a length, width and thickness wherein the length, width and thickness of each of said support plates is about the same as the length, width and thickness of said top plate; each of said support plates having an about elliptical opening that has a major axis coincidental with the centerline of said length; said top plate and said plurality of support plates being stacked and interconnected to form an elliptical bumper opening for receiving the upper region of said elastomeric bumper;
g. said lower ankle bumper fixture having a length, width and thickness forming an about elliptical surface having about the same size as said elliptical bumper opening and having a lip about the periphery of said elliptical surface, said lip extending vertically upward along the sides and vertically upward and radially outward along the ends;
h. said elastomeric bumper having a length, width and thickness having an about elliptical cross section when said cross section is taken on a horizontal plane and about flat upper and lower about elliptical surfaces lying in respective horizontal planes;
i. said height of said elastomeric bumper being greater than the combined thickness of all of said plurality of support plates and the height of said lip;
j. the upper region of said elastomeric bumper being positioned in said elliptical bumper opening of said upper ankle bumper fixture, said upper surface of said elastomeric bumper abutting and being fixedly attached to said top plate of said upper ankle bumper fixture, said lower surface of said elastomeric bumper abutting, being vertically supported by, and being fixedly attached to said lower ankle bumper fixture, and said lower region of said elastomeric bumper being laterally supported by said lip of said lower ankle bumper fixture;
k. said foot being made of flexible foam material and having a cavity formed in the upper region thereof, said bumper assembly being positioned within said cavity wherein said upper ankle bumper fixture is in wedged contact with said foot adjacent to the upper region of said cavity;
l. said shin block, foot, top plate, elastomeric bumper and lower ankle bumper fixture each having an opening for receiving said cable assembly, said openings having coincidental centerlines;
m. said cable assembly positioned within said openings for rigidly interconnecting said shin block, foot and bumper assembly; whereby
n. transverse rotary motion of said foot about the long axis of the shin is allowed when externally applied torque exceeds the opposing, resistive force of said elastomeric bumper; and the restorative force of said elastomeric bumper causes said foot to tend to return to its original at-rest orientation with respect to the long axis of the shin when said externally applied torque is lessened.

* * * * *